US011112145B2

(12) United States Patent
Liu et al.

(10) Patent No.: US 11,112,145 B2
(45) Date of Patent: Sep. 7, 2021

(54) ARTIFICIAL PLATELETS FOR TREATING CATASTROPHIC BLEEDING

(71) Applicant: The Board of Trustees of the University of Illinois, Urbana, IL (US)

(72) Inventors: Ying Liu, Claredon Hills, IL (US); Alexander Donovan, Glencoe, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 325 days.

(21) Appl. No.: 15/513,752

(22) PCT Filed: Sep. 24, 2015

(86) PCT No.: PCT/US2015/051814
§ 371 (c)(1),
(2) Date: Mar. 23, 2017

(87) PCT Pub. No.: WO2016/049250
PCT Pub. Date: Mar. 31, 2016

(65) Prior Publication Data
US 2018/0180328 A1   Jun. 28, 2018

Related U.S. Application Data

(60) Provisional application No. 62/054,461, filed on Sep. 24, 2014.

(51) Int. Cl.
| | |
|---|---|
| *F25B 9/04* | (2006.01) |
| *A61K 38/36* | (2006.01) |
| *A61K 9/127* | (2006.01) |
| *A61P 7/04* | (2006.01) |
| *A61K 33/42* | (2006.01) |
| *F16K 49/00* | (2006.01) |
| *G05D 23/19* | (2006.01) |

(52) U.S. Cl.
CPC .............. *F25B 9/04* (2013.01); *A61K 9/1271* (2013.01); *A61K 9/1278* (2013.01); *A61K 33/42* (2013.01); *A61K 38/36* (2013.01); *A61P 7/04* (2018.01); *F16K 49/005* (2013.01); *G05D 23/1919* (2013.01)

(58) Field of Classification Search
CPC ...................................................... A61K 9/127
See application file for complete search history.

(56) References Cited

U.S. PATENT DOCUMENTS

| | | | | |
|---|---|---|---|---|
| 5,340,587 | A * | 8/1994 | Mihalko | A61K 9/0078 424/45 |
| 5,512,295 | A * | 4/1996 | Kornberg | A61K 9/127 264/4.1 |
| 2002/0045263 | A1 | 4/2002 | Leong et al. | 435/455 |
| 2010/0129430 | A1* | 5/2010 | Sofou | A61K 9/1271 424/450 |
| 2011/0150984 | A1* | 6/2011 | Veldman | A61K 9/0019 424/450 |
| 2012/0201872 | A1 | 8/2012 | Huang et al. | 424/450 |
| 2013/0273561 | A1* | 10/2013 | Walker | G01N 33/54373 435/7.2 |
| 2016/0184340 | A1* | 6/2016 | Kritikou | A61K 31/7048 424/450 |

FOREIGN PATENT DOCUMENTS

| | | |
|---|---|---|
| CN | 104010627 | 8/2014 |
| WO | 2006/096345 A2 | 9/2006 |
| WO | 2012/048271 A1 | 4/2012 |

OTHER PUBLICATIONS

Morrissey et al (Blood 119:5972-5979, 2012) (Year: 2012).*
Papahadjopoulos et al. "Sterically Stabilized Liposomes: Improvements in Pharmacokinetics and Antitumor Therapeutic Efficacy" *Proceedings of the National Academy of Sciences USA* 1991 88:11460-11464.
Ransom, R. "Developing Polyphosphate Bound Nanoparticles for Inducing Quick Blood Clotting" 2004 Master's Thesis, University of Illinois at Chicago.
Ruiz et al., "Human Platelet Dense Granules Contain Polyphosphate and are Similar to Acidocalcisomes of Bacteria and Unicellulary Eukaryotes" *The Journal of Biological Chemistry* 2004 42:44250-44257.
Smith et al. "Polyphosphate Modulates Blood Coagulation and Fibrinolysis" 2006 *Proceedings of the National Academy of Sciences USA* 103:903-908.
Torchilin, V.P. "Recent Advances with Liposomes as Pharmaceutical Carriers" 2005 *Nature Reviews Drug Discovery* 4:145-160.
International Search Report and Written Opinion dated Dec. 28, 2015 in PCT/US2015/051814.
International Preliminary Report on Patentability dated Apr. 6, 2017 in PCT/US2015/051814.

* cited by examiner

*Primary Examiner* — Craig D Ricci
(74) *Attorney, Agent, or Firm* — Licata & Tyrrell P.C.

(57) ABSTRACT

Artificial dense granules composed of a sterically stabilized liposome shell encapsulating a polyphosphate nanoparticle core are provided as are methods for their production and use in the treatment of a severe hemorrhagic event.

6 Claims, 5 Drawing Sheets

ARTIFICIAL PLATELETS FOR TREATING CATASTROPHIC BLEEDING

This application is a U.S. National Stage Application of PCT/US2015/051814 filed Sep. 24, 2015 and claims the benefit of priority of U.S. Provisional Application No. 62/054,461, filed Sep. 24, 2014, the contents of each of which are incorporated herein by reference in their entirety.

This invention was made with government support under contract number W81XWH-11-2-0021 awarded by the Department of Defense. The government has certain rights in the invention.

BACKGROUND

Hemorrhagic events arising from trauma in either the civilian or military setting contribute to a significant proportion of avoidable fatality. In countless combat scenarios proper management of hemorrhage is not immediately feasible without invasive surgical intervention, with topical hemostatic wound dressings and other pharmacological agents, which can be delivered on-demand on the battlefield, being therapeutically inferior in mitigating internal, incompressible bleeding sources. Clinical guidelines created to diminish poor outcomes in patients experiencing an uncontrolled post-traumatic bleeding event instead have focused more globally on general stabilizing measures designed to restore normal circulatory perfusion to the wounded after swiftly determining and suppressing the source of bleeding by a trained clinician rather than via administration of a hemostat as a first-line therapy.

However, these guidelines have largely failed to eradicate trauma-related complications even in industrialized countries and both private and public entities have invested heavily into the research and development of a targeted, on-demand, broad-spectrum procoagulant agent. The Food and Drug Administration (FDA) has approved a myriad of pharmacological therapies in recent years to address external compressible trauma, enhancing survival and reestablishing hemostasis without surgery. HEMCON®, for example, is a commercially available bandage composed of a biodegradable polysaccharide, chitosan, which rapidly marginates negatively charged erythrocytes at the trauma site due to the macromolecule's high positive charge density. Nonetheless, HEMCON® and all the other presently available therapies, fail to be effective for the treatment of incompressible wounds, therefore necessitating time-critical, invasive care in hospital.

Nanoscale drug delivery has emerged as a novel therapeutic platform in recent decades with the potential to drastically transform medical treatment, promising reduced side effects, enhanced efficacy, and therapeutic delivery to only effected organs and tissues. Design of new treatments has entailed the encapsulation of therapeutic agents into colloidal particles such as phospholipid vesicles (Torchilin (2005) Nat. Rev. Drug Discov. 4:145-60), polymersomes, viral capsids, polymeric micelles, and other self-assembled nanostructures≤200 nm in diameter. Among these candidate drug architectures, vesicles have been approved by the FDA to treat a number of disorders, especially cancer. The liposomal envelope, which contains a small molar percentage of poly(ethylene glycol)-phosphatidylethanolamine (PEG-PE), is used for steric stabilization and long blood circulation time (Papahadjopoulos, et al. (1991) Proc. Natl. Acad. Sci. USA 88:11460-11464).

Given both the limitations of the available treatments to achieve hemostasis and the promise of nanotherapeutics, numerous candidate nanoparticle hemostats have been developed in recent years. These nanotherapeutics attempt to imitate at least some aspects of platelet morphology and the procoagulant response adjacent to the bleeding site; however, most fail to mimic the threshold-switchable behavior necessary to establish hemostasis without deleterious ramifications. For example, platelet-like nanoparticles (PLNs), synthesized by alternative deposition of the polyelectrolytes, bovine serum albumin (BSA) and poly(allylamine) hydrochloride on a polystyrene (PS) core nanoparticle have been described. Further functionalization of the PLN with targeting peptide ligands allow PLNs to accumulate at the bleeding site, bind and interact synergistically with the body's own activated platelets, and rapidly induce coagulation at the site of trauma. However, the synthesis of the PLNs involves multiple steps and nonbiodegradable polystyrene.

Inorganic polyphosphate (polyP), on the contrary, is virtually omnipresent in biology and degradable in human blood plasma on therapeutic time scales. The polymer is a highly negatively charged macromolecule of orthophosphates and is often stored intracellularly in a precipitated form as 100-300 nm granules in conjunction with calcium and other divalent and multivalent cations. These organelles, generally termed "acidocalcisomes," are present in all species including humans. These subcellular phosphate-containing bodies are called dense granules in human platelets due to their uniformly high electron density. Their contents are secreted upon platelet activation, where they exert potent procoagulant and proinflammatory effects, especially on Factor V and thrombin-promoted Factor XI activation.

Approaches for using polyphosphate for blood clotting have been described. For example, Smith, et al. ((2006) Proc. Natl. Acad. Sci. USA 103:903-908) describe polyphosphate as a potent hemostatic regulator, accelerating blood clotting by activating the contact pathway and promoting the activation of factor V, which in turn results in abrogation of the function of the natural anticoagulant protein, tissue factor pathway inhibitor. Further, WO 2012/048271 describes derivatized inorganic polyphosphate molecules and use of the same for reducing bleeding in a patient. WO 2006/096345 describes a composition for promoting clotting composed of tissue factor, a phospholipid and polyphosphate and a method of using the same to stop or slow bleeding from a wound. Ransom ((2014) "Developing Polyphosphate Bound Nanoparticles for Inducing Quick Blood Clotting," Master's Thesis, University of Illinois at Chicago) describes the development of nanoparticles containing distinct numbers of polyP chains bound to a core composed of G4 PAMAM dendrimer, polystyrene, or gold nanoparticles and use of the same for blood clotting. In addition, US 2002/0091230 describes the use of biodegradable terephthalate polymers containing phosphate linkages for delivering coagulation agents.

SUMMARY OF THE INVENTION

The present invention provides artificial dense granules comprising or consisting of a sterically stabilized liposome shell encapsulating a polyphosphate nanoparticle core. In some embodiments, the polyphosphate of the nanoparticle core has between 50 and 125 repeating phosphate units. In other embodiments, the polyphosphate of the nanoparticle core has at least 100 repeating phosphate units. In further embodiments, the sterically stabilized liposome shell is composed of a PEGylated glycerophospholipid, and can further include a phospholipid, a sterol, a polymer-lipid, an amine-functionalized lipid or polymer, or a derivative or combination thereof. In particular embodiments, the sterically stabilized liposome shell is composed of phosphatidylcholine and 1,2-di-palmitoyl-sn-glycero-3-phosphoethanolamine-N-[methoxy (polyethylene glycol)-2000].

The present invention also provides a method for preparing artificial dense granules by precipitating polyphosphate under aqueous conditions at physiologic pH and salt conditions to form nanoparticles; preparing sterically stabilized liposomes; combining the nanoparticles and sterically stabilized liposomes; and agitating the combination to prepare artificial dense granules. In some embodiments, the physiologic pH is in the range of 5.0 to 7.5; the physiologic salt is calcium chloride, magnesium chloride, zinc chloride or a combination thereof; and the physiologic salt is at a concentration in the range of 1.2 mM to 5.0 mM. In certain embodiments, the physiologic salt is 5 mM calcium chloride, or 1.2 mM calcium chloride and 0.4 mM magnesium chloride. In other embodiments, the polyphosphate is between 50 and 125 repeating phosphate units or at least 100 repeating phosphate units. In further embodiments, the sterically stabilized liposomes are composed of a PEGylated glycerophospholipid and can further include a phospholipid, a sterol, a polymer-lipid, an amine-functionalized lipid or polymer, or a derivative or combination thereof. In certain embodiments, the sterically stabilized liposomes are composed of phosphatidylcholine and 1,2-di-palmitoyl-sn-glycero-3-phosphoethanolamine-N-[methoxy (polyethylene glycol)-2000]. A kit for preparing the artificial dense granules is also provided as is a method for treating a severe hemorrhagic event using the artificial dense granules.

BRIEF DESCRIPTION OF THE DRAWINGS

FIG. 5 shows the verification of the ADG encapsulation efficiency by measuring ADG diameter shifts after exposure to detergent and changes in calcium concentration. Liposome solubilization by the non-ionic detergent TWEEN 20, in conjunction with an increase in the calcium concentration, was exploited to judge the ADG encapsulation efficiency semi-quantitatively. In the absence of TWEEN 20 and an increase in calcium concentration to 7.5 mM at t=30 minutes, there is no statistically significant perturbation in the ADG effective diameter. However, increasing the calcium concentration after dissolution of the lipid envelope by detergent exposure allows for the granular nanoparticles to be exposed to the higher amount of calcium, resulting in an increased effective diameter as the thermodynamic equilibrium is shifted.

FIG. 7 shows FXII autoactivation after preincubation with phospholipase C (PLC) from C. perfringens. ADGs were digested with 10.6 µg/ml PLC at 37° C. for 20 minutes before initiation of FXII autoactivation. Bare polyP nanoparticles with BSA show no FXII autoactivity, whereas ADGs preincubated with PLC manifest a similar rate of absorbance increase to ADCs solubilized with TWEEN 20. ADGs without PLC do not measureably promote FXII autoactivation at the concentration tested. Empty liposomes digested with PLC show some absorbance increase, which is likely a result of vesicle aggregation after phospholipid hydrolysis. Bare polyP nanoparticles without 0.1% BSA were included as a positive control. a, assay buffer only; b, 500 µM bare polyP NP without BSA; c, 500 µM bare polyP NP with BSA; d, ADG; e, ADG+10.6 µg/ml PLC; f, empty liposomes; and g, empty liposomes+10.6 µg/ml PLC.

FIG. 8 shows the contact activity of ADGs in citrated pooled normal plasma (PNP) upon triggered release of polyP by PLC-induced hydrolysis. Activator (no activator, bare polyP NP, ADG, ADG+PLC) was added immediately to recaclified, citrated PNP and initiation of the contact pathway was assayed by turbidity increase at 405 nm. Fifty µM bare polyP NPs are modest contact activators, with the time to clot initiation at ~15-20 min. Fifty µM ADGs+30 µg/ml PLC, on the other hand, are excellent procoagulant agents, clotting in about 10 minutes. Fifty µM ADGs without trigger manifest some procoagulant effect roughly equal to the bare particles. As the initiation of the contact pathway requires the colocalization of three proteins on the same surface, the rate follows a U-shaped kinetic profile. Further reducing the concentration may reduce the procoaguability of the "ADGs without trigger molecules (such as PLC)" without affecting the efficacy of "ADGs with trigger molecules." a, control (5 mM Ca$^{2+}$); b, 50 µM bare polyP NPs; c, 50 µM ADGs; d, 50 µM ADGs+30 µg/ml PLC.

DETAILED DESCRIPTION OF THE INVENTION

Figure 1:
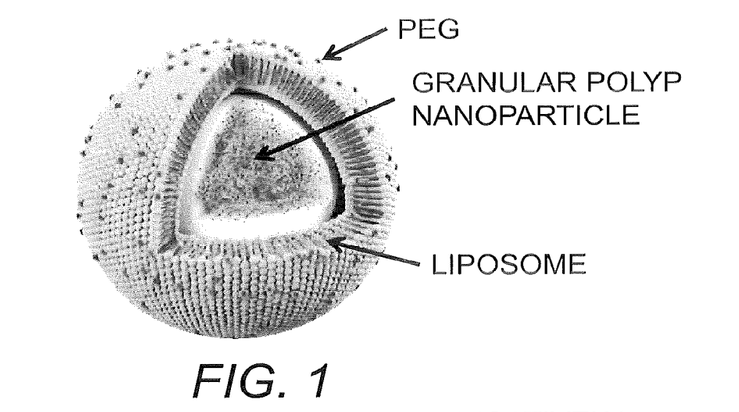
FIG. 1 shows the design and structure of an artificial dense granule (ADG) of the invention. ADGs are about 150-nm granular polyP nanoparticles encapsulated in about 200-nm sterically stabilized liposomes modeled after human platelet dense granules.

A polyP-based liposomal particle, referred to herein as an "artificial dense granule" or "ADG" (FIG. 1), has now been developed for use as a procoagulant nanotherapy imitating human platelet dense granules. High-resolution Transmission Electron Microscopy and electron energy loss spectrum imaging of ADGs confirm the nanostructure of a 200-nm sterically stabilized liposome shell encapsulating a 150-nm diameter granular polyP nanoparticle core. A biocompatible, label-free direct graphene sandwich approach was used in electron microscopy experiments to prevent beam-induced mass loss and morphology change. Light scattering measurements of ADGs in suspension indicate that the nanoparticle hemostat is colloidally stable. Triggered initiation of FXII autoactivation by ADGs via detergent solubilization or phospholipase hydrolysis of the liposomal envelope in an in vitro model indicates that the artificial dense granules of the invention are of use in activating the contact system of clotting to limit blood loss following a severe hemorrhagic event.

As is known in the art, platelet dense granules, also known as dense bodies or delta granules, are specialized secretory organelles containing adenosine diphosphate (ADP), adenosine triphosphate (ATP), ionized calcium, histamine and serotonin. The instant artificial dense granule mimics certain features of platelet dense granules by providing polyphosphate and calcium, which is necessary for several steps of the coagulation cascade.

The artificial dense granules of the present invention are composed of a sterically stabilized liposome shell encapsulating a granular platelet-sized polyphosphate nanoparticle core. A "polyphosphate nanoparticle core" refers to a precipitated particle of polyphosphate that is between 100 and 250 nm in diameter, or more preferably about 150 nm in diameter. As demonstrated herein, the elemental composition of the nanoparticle core is composed of Ca, P and O. In certain embodiments, the nanoparticle has a P:Ca ratio of approximately 2:1.

PolyP refers to a compound of the following formula:

where the value of n is equal to the number of $PO_3$ units in the molecule and n is at least 3. Also included are salts, esters, and anhydrides of polyphosphate, as well as cyclic polyphosphates. Concentrations of polyphosphate and any polyP may be expressed as "phosphate equivalents," which means the concentration of $PO_3$ moieties (for example, 1 μM $polyP_{75}$ is the same as 75 μM phosphate equivalents of $polyP_{75}$). All amounts and concentrations of polyP are expressed herein as phosphate equivalents. In certain embodiments of this invention, the polyP of the nanoparticle core has between 50 and 125 repeating phosphate units or phosphate equivalents. In other embodiments, polyP of the nanoparticle core of the invention has at least 100 repeating phosphate units and as many as 1000, 2000, 3000, 4000, or 5000 repeating phosphate units.

The polyphosphate nanoparticle core may be produced as demonstrated herein by precipitating polyp under aqueous conditions at physiologic pH (e.g., a pH of ~7 or the pH in the inside of a human platelet dense granule, i.e., ~pH 5.5) and salt conditions. In particular, the polyP is mixed with a divalent or polyvalent metal ion, e.g., calcium chloride or a combination of calcium chloride and magnesium chloride, in an aqueous solution having a pH in the range of 5.0 to 7.5, or more preferably 5.4 to 7.4. Upon agitation, e.g., vortexing, the polyP precipitates to form the nanoparticle core. As shown herein, physiologic salt concentrations facilitated the precipitation of polyP. Accordingly, in certain embodiments, the salt is used at a concentration in the range of 1.2 mM to 5.0 mM. In particular embodiments, the polyP nanoparticle core is produced using 5 mM calcium chloride. In other embodiments, the polyP nanoparticle core is produced using 1.2 mM calcium chloride and 0.4 mM magnesium chloride. In a further embodiment, the polyP nanoparticle core is produced using magnesium chloride or magnesium chloride in combination with at least one other salt of a divalent metal, e.g., zinc, iron, copper, iron, manganese, nickel, tin, etc. As a further alternative, the polyP nanoparticle core may be produced by precipitation of the polyP using solvent exchange in a size-controlled manner.

Sterically stabilized liposomes (SSLs)(also known as PEG-liposomes) are polymer-coated liposomes, wherein the polymer, e.g., polyethylene glycol (PEG), is covalently conjugated to one of the phospholipids or polymers and provides a hydrophilic "cloud" outside the liposomal shell. This steric barrier delays the recognition by opsonins, allowing SSLs to remain in the blood circulation much longer than conventional liposomes and increases the pharmacological efficacy of encapsulated agents. The mechanism by which SSLs avoid macrophages and circulate longer in the blood is thought to involve the formation of a "steric barrier" around the liposomes by the attached PEG molecules. The circulation time of SSLs may be controlled by selection of their size, PEG molecular weight, chain length and concentration and selection of the lipid composition. See, for example, Rubenstein, et al. (2006) Int. J. Pharm. 316(1-2):144-147.

Polymers of the liposomes of the invention can include any compound known and routinely utilized in the art of sterically stabilized liposome technology and technologies that are useful for increasing circulatory half-life for proteins, including for example polyvinyl alcohol, polylactic acid, polyglycolic acid, polyvinylpyrrolidone, polyacrylamide, polyglycerol, polyaxozlines, or synthetic lipids with polymeric head groups. In some embodiments, the polymers are water-soluble polymers. Such water soluble polymers include, but are not limited to, polyethylene glycols, copolymers of ethylene glycol/propylene glycol, polyvinyl alcohol, carboxymethylcellulose, polyvinyl pyrrolidone, poly-1,3-dioxolane, poly-1,3,6-trioxane, ethylene/maleic anhydride copolymer, polyaminoacids (either homopolymers or random copolymers), and dextran.

In certain embodiments, a polymer of the invention is polyethylene glycol or "PEG." In some embodiments, a "PEG" is a polyalkylene glycol compound or a derivative thereof, with or without coupling agents or derivatization with coupling or activating moieties (e.g., with aldehyde, hydroxysuccinimidyl, hydrazide, thiol, triflate, tresylate, azirdine, oxirane, orthopyridyl disulphide, vinylsulfone, iodoacetamide or a maleimide moiety). "PEG" includes substantially linear, straight chain PEG, branched PEG, or dendritic PEG. See, e.g., U.S. Pat. Nos. 5,171,264; 5,932, 462; 6,602,498.

PEG is a well-known, water-soluble polymer that is commercially available or can be prepared by ring-opening polymerization of ethylene glycol according to methods well known in the art. In the present application, the term "PEGylated" or "PEG" is used broadly to encompass any polyethylene glycol molecule, in mono-, bi-, or poly-functional form, without regard to size or to modification at an end of the PEG, and can be represented by the formula, X—O(CH$_2$CH$_2$O)—OH, where n is 20 to 2300 and X is H or a terminal modification, e.g., an alkyl. In some useful embodiments, a PEG used in the invention terminates on one end with hydroxy or methoxy, i.e., X is H or CH$_3$ ("methoxy PEG"). It is noted that the other end of the PEG, which is shown in the formula above terminating in OH, covalently attaches to an activating moiety via an ether oxygen bond, an amine linkage, or amide linkage. When used in a chemical structure, the term "PEG" includes the formula above without the hydrogen of the hydroxyl group shown, leaving the oxygen available to react with a free carbon atom of a linker to form an ether bond.

Any molecular mass for a PEG can be used as practically desired, e.g., from about 1,000 Daltons (Da) to 100,000 Da (n is 20 to 2300). In one aspect, "PEG" at a molecular weight between 1000 Da and 5000 Da is used in the invention. The number of repeating units "n" in the PEG is approximated for the molecular mass described in Daltons.

Molecules for producing the liposomes/polymersomes of the invention can include a lipid such as a phospholipid, a sterol such as cholesterol, polymer-lipid, amine-functionalized lipid or polymer, amphiphilic peptide, polyelectrolyte, amphiphilic copolymer (block, graft etc.), or a derivative or combination thereof, which is of biomedical or therapeutic use and forms an impermeable barrier. Exemplary liposome polymers include, but are not limited to cholesterol, sphingomyelin or natural or synthetic phospholipids, such as phosphatidylcholine (soybean phosphatidylcholine, yolk phosphatidylcholine, distearoyl phosphatidylcholine, dipalmitoyl phosphatidylcholine, etc.), phosphatidylethanolamine (distearoyl phosphatidylethanolamine, dipalmitoyl phosphatidylethanolamine, etc.), phosphatidylserine, phosphatidic acid, phosphatidylglycerol, phosphatidylinositol, lysophosphatidylcholine, sphingomyelin, yolk lecithin, soybean lecithin, hydrogenated phospholipid, and the like. Among these, it is preferable to use a phospholipid having a phase transition temperature higher than in vivo temperatures (35° to 37° C.) In some embodiments, cholesterol or other lipids such as sphingomyelin or high-melting temperature saturated glycerophospholipids (e.g., Hydrogenated soybean phosphatidylcholine) may be used in the instant liposome to reduce dilution-dependent effects, prevent premature leakage, and/or enhance membrane rigidity. In certain embodiments, the liposome includes a glycerophospholipid such as 1,2-dipalmitoyl-sn-glycero-3-phosphoethanolamine (DPPE), 1,2-Didecanoyl-sn-glycero-3-phosphocholine (DDPC), 1,2-Dipalmitoyl-sn-glycero-3-phosphocholine (DPPC), and the like. In particular embodiments, the glycerophospholipid is a PEGylated glycerophospholipid, i.e., a glycerophospholipid covalently bonded to PEG (e.g., PEG-DPPE or PEG-DPPC). These lipids may be used alone or in combination.

When the lipids are used in combination, the liposome is preferably composed of at least two components, one being a PEGylated glycerophospholipid such as PEG-DPPE, PEG-DDPC, or PEG-DPPC; and the second being a phospholipid selected from phosphatidylcholine, phosphatidylserine, phosphatidylglycerol, phosphatidylethanolamine, or a combination thereof. In certain embodiments, the lipids of the liposome are phosphatidylcholine and 1,2-di-palmitoyl-sn-glycero-3-phosphoethanolamine-N-[methoxy (polyethylene glycol)-2000].

In addition to lipids, it is contemplated that any compound or protein, which forms a complex or association with polyP, or is able to encapsulate polyP following the equivalent agitation process, e.g., polyamines, serum albumin, polymersomes, polypeptide vesicles, or polyelectrolyte vesicles, may be used to encapsulate or deliver polyp to the bleeding site in a targeted manner.

Methods for preparing the sterically stabilized liposomes of the invention can be carried out using any of the various techniques known in the art, including agitation, sonication, extrusion, solvent exchange, evaporation, etc. By way of illustration, liposome components are mixed in an organic solvent and the solvent is removed using either evaporation or lyophilization. Removal of the organic solvent results in a lipid film, or cake, which is subsequently hydrated using an aqueous solution to permit formation of liposomes.

To prepare the artificial dense granules of the invention, the sterically stabilized liposomes are combined with the polyP nanoparticles and the combination is agitated. Once the polyP nanoparticles associate with the liposomes, the artificial dense granules are formed. In certain embodiments, the combined sterically stabilized liposomes and polyphosphate nanoparticles form unilamellar vesicles of sizes from 150 to 250 nm or more preferably about 200 nm. Preferably the composition is prepared to have substantially homogeneous sizes in a selected size range, with the average diameter typically being about 200 nm. One method for obtaining the desired size is extrusion of the composition through polycarbonate membranes having pores of a selected size, such as about 200 nm.

To facilitate the preparation of the instant artificial dense granules, this invention also provides a kit. In its simplest form, the kit is composed of a polyphosphate component, a salt component and a lipid component. More specifically, the kit is composed of a polyphosphate component, which includes a polyphosphate and an aqueous solution at physiologic pH (e.g., a pH of ~7 or the pH in the inside of a human platelet dense granule, i.e., ~pH 5.5), or an aqueous polyphosphate solution at physiologic pH; a salt component, which includes calcium chloride or calcium chloride and magnesium chloride; and a lipid component, which includes sterically stabilized liposomes or a PEGylated glycerophospholipid and a phosphatidylcholine, a phosphatidylserine, a phosphatidylethanlamine, a phosphatidylglycerol, or a combination thereof, wherein each component is provided in at least one container. For example, the kit can include an aqueous polyphosphate solution at physiologic pH in one container, calcium chloride or calcium chloride and magnesium chloride in a second container, and sterically stabilized liposomes in a third container. Alternatively, the kit can include multiple containers for each component. For example, such a kit can include polyphosphate in one container, an aqueous solution at physiologic pH in a second container, calcium chloride or calcium chloride and magnesium chloride in a third container, and sterically stabilized liposomes in a fourth container. The kit can also contain other solutions necessary or convenient for carrying out the invention. The container can be made of glass, plastic or foil and can be a vial, bottle, pouch, tube, bag, etc. The kit may also contain written information, such as procedures for carrying out the present invention or analytical information, such as the amount of reagent contained in the container means. The container can be in another container, e.g., a box or a bag, along with the written information.

One of polyP's hemostatic mechanisms of action is that it triggers the contact pathway of blood clotting and autoactivates the FXII zymogen. Therefore, the artificial dense granules of this invention find application in a method for treating a severe hemorrhagic event. Such a method involves administering to a subject in need of treatment an effective amount of the artificial dense granules of the invention, e.g., a pharmaceutically acceptable carrier such as buffer or saline, to activate the contact pathway of coagulation and treat the subject's severe hemorrhagic event. The method of the invention can be used to treat hemorrhagic events arising from trauma in either the civilian or military setting or to treat hemophilia, either by chronic administration, or by acute administration to treat a bleeding episode. The artificial dense granules can also be used to treat other coagulation deficient patients, such as those suffering from liver failure and acquired hemophilia. In addition, prophylactic administration of the artificial dense granules can be used prior to surgery or other activities where a coagulation deficient patient would be at risk of a bleeding episode.

Administration of the artificial dense granules can also be used to reduce the effects of anticoagulant therapy, and treat poisoning by anticoagulants. Examples of anticoagulants include low molecular weight heparins such as enoxaparin (LOVENOX®), dalteparin (FRAGMIN®) and tinzaparin (INNOHEP®); heparin; heparinoids such as danaparoid (ORGARAN®); pentasaccharides such as fondaparinux (ARIXTRA®); as well as argatroban, warfarin (COUMADIN®) and rivaroxaban (XARELTO®).

The artificial dense granules of the invention can be administered alone or in combination with other agents to facilitate release of the polyP nanoparticle core or provide additional therapeutic agents. In some embodiments, the liposomal shell is chemically modified with other biocompatible polymers and/or peptides to further enhance drug targeting and drug half-life. Moreover, any triggering mechanism can be used for drug delivery, including, e.g., hydrolysis of the lipid envelope. For example, enzymes present at the wound site, e.g., secretory phospholipase A2 (sPLA2), which is elevated in blood around trauma sites, can preferentially degrade and/or bind with the functionalized surface of the artificial dense granules to facilitate interaction with other activated platelets and enhance therapeutic efficacy and avoid unspecific blood coagulation. In particular, the ADGs of this invention can be functionalized with proteins, antibodies or antigens such as fibrinogen, integrin (e.g., p-selectin), or collagen, which in conjunction with phospholipase hydrolysis, promote hemostasis and recruit endogenous activated platelets. The surface of the ADCs can be functionalized using simple, established chemistries already known in the art, e.g., maleimide chemistry.

The artificial dense granules can be administered to the site from which bleeding occurs as part of a dressing, bandage, chitosan material, collagen sponge, or gelatin scaffold. Alternatively, the artificial dense granules can be formulated for topical application in a gel, cream, or ointment or other material, as appropriate to the intended use and as readily apparent to one of skill in the art. Further, the artificial dense granules can be administered intravenously as a suspension including a pharmaceutically acceptable carrier, such as saline. The artificial dense granules can be administered as an injection, for example intravenously, intraperitoneally, subcutaneously or intramuscularly. Administration over a longer period of time may be accomplished by implanting a controlled release device, by injection of the artificial dense granules in a controlled or extended release pharmaceutically acceptable carrier, or transdermally. Preferably, the artificial dense granules and solutions of artificial dense granules are sterile. Preferably, administration is by saline bolus or continuous infusion.

The following non-limiting examples are provided to further illustrate the present invention.

Example 1

Material and Methods

Materials and Reagents. Tris(hydroxymethyl) aminomethane, $CaCl_2 \cdot 6H_2O$, $MgCl_2 \cdot 6H_2O$, NaCl, KCl, and bovine serum albumin (BSA) were purchased from Sigma-Aldrich (St. Louis, Mo.). Water was de-ionized to 18.2 MΩ-cm (Nanopure II, Bamstead, Dubuque, Iowa). Citrated, pooled normal plasma was purchased from George King Bio-medical (Overland Park, Kans.). 1,2-di-palmitoyl-sn-glycero-3-phosphoethanolamine-N-[methoxy (polyethylene glycol)-2000](ammonium salt)($PEG_{2k}PE$), L-α-phosphatidylcholine (PC), L-α-phosphatidylserine (PS), and AVANTI Mini-Extruder with 200-nm pore diameter polycarbonate membrane were purchased from AVANTI Polar Lipids (Alabaster, Ala.). All materials were purchased at standard grades and used as received. Polyphosphate (polyP) was size fractionated via preparative electrophoresis as previously described (Smith, et al. (2010) *Blood* 116:4353-9), or by differential isopropanol precipitation of heterogeneous long chain polyP. Materials used were polyP80 (76-84 repeating units), polyP250, (100-390 repeating units), polyP305 (242-383 repeating units), polyP1000+(more than 1000 repeating units), or Natriumpolyphosphat P70 (BKGP70, approximate range 50-125 repeating units) from BK Guilini GmbH (Ludwigshafen am Rhein, Germany). PolyP concentrations are given throughout in terms of the concentration of phosphate monomer (monoP).

PolyP Nanoprecipitation. Aqueous size-fractionated polyP was micropipetted into 8 mM Tris•HCl, pH 7.4 solutions containing combinations of the following: 1.2 mM, 5.0 mM, or 7.5 mM $CaCl_2$; 0.4 mM $MgCl_2$; 4.35 mM KCl; and 150 mM NaCl. The nanoparticles were then vortexed for five seconds. Precipitation was characterized by dynamic light scattering (DLS) (Brookhaven NanoDLS, Brookhaven, N.Y.).

Determination of PolyP Solubility. Measurements of polyP solubility were similar to the procedure used to determine the critical micelle concentration (CMC) of surfactants, copolymers, and phospholipids using DLS. PolyP samples were prepared as described above and injected into the DLS, beginning at exceedingly low concentrations (typically 100 nM-1 µM monoP), where the scattering count rate resembled that of molecularly dissolved polyP. The polyP concentration was slowly titrated up until the scattering count rate increased and the correlation function was a well-behaved exponential decay on the baseline, suggesting that the polyP sample was supersaturated. The scattering count rate was then plotted against the logarithm of the monoP concentration, producing a plot with two clear regimes representing: (1) molecularly dissolved polyp, and (2) precipitated polyP. A linear regression was then performed on each regime and the point of intersection was found, which was defined as the solubility concentration. For consistency, all measurements were done on low laser intensity.

PolyP Nanoparticle (NP) Stability in Aqueous Buffer. NPs were synthesized using polyP250 (125 µM) in either 1.2 mM or 5 mM $CaCl_2$ buffered with 8 mM Tris•HCl, pH 7.4 as discussed previously. Immediately after vortexing, particle size was characterized by DLS using at least a one-minute scattering time every five minutes for 1 hour at room temperature.

PolyP NP Stability in Bovine Serum Albumin (BSA) Suspensions. A solution of BSA (70 mg/ml) containing 8 mM Tris•HCl, pH 7.4 was prepared both with and without 2.5 mM CaCl$_2$ the day before experiments were conducted. PolyP250 (125 µM) was nanoprecipitated in 5 mM CaCl$_2$, 8 mM Tris•HCl, pH 7.4, and the particle diameter was determined immediately by DLS. The polyP NPs were then mixed 1:1 (v:v) with the BSA suspensions. The resulting BSA and CaCl$_2$ concentrations were thus 35 mg/ml and 1.25 mM, respectively. Particle size was measured using DLS every five minutes for 1 hour, and subsequently every 30 minutes until three hours had elapsed. The dispersion viscosity was calculated to be 1.2 centipoise (Einstein (1906) *Ann. Phys.* 19:289-306), and the refractive index was kept the same as water (1.331).

Transmission Electron Microscopy (TEM). PolyP250 (125 µM) was nanoprecipitated in 5 mM CaCl$_2$, 8 mM Tris•HCl, pH 7.4 as described above. The sample (10 µl) was micropipetted onto a 300-mesh carbon-coated Formvar grid and allowed to dry in air for 10 minutes. The remaining liquid was wicked away with a lint-free paper towel and the process was repeated two more times to increase particle density and minimize aggregation. The sample was viewed in a JEOL JEM-1220 Transmission Electron Microscope (JEOL, Japan).

For X-ray microanalysis, polyP250 NPs (10 µl) were micropipetted onto a 300-mesh Holey carbon grid. The sample was dried for 15 minutes and examined in a JEOL JEM-3010 Transmission Electron Microscope (JEOL, Japan).

Preparation of Platelet polyP at High Supersaturation Ratio at Acidic pH. Aqueous (dissolved) polyphosphate was precipitated in aqueous 5 mM CaCl$_2$, pH 5.4. Briefly, the polyphosphate was micropipetted into the calcium solution and vortexed for 5 seconds. Polyphosphate precipitated at supersaturation ratios exceeding 100 were diluted with more 5 mM CaCl$_2$, pH 5.4 prior to DLS characterization. Dilution should not alter NP effective diameter as it is hysteric.

Preparation of Large Unilamellar Vesicles (LUV). Sterically-stabilized LUV (200 nm) composed of 95 mol % PC/5 mol % PEG$_{2k}$PE were synthesized via extrusion through a 200-nm pore-diameter polycarbonate membrane (Mui, et al. (2002) *Methods Enzymol.* 367:3-14). Briefly, 14.3 µl of 25 mg/mL PEG$_{2k}$PE and 76.1 µl of 25 mg/mL PC (both dissolved in chloroform) were micropipetted into a 7 mL glass scintillation vial and dried under a gentle stream of argon gas. The dried lipid film was then placed under vacuum for an additional sixty minutes to remove any residual traces of organic solvent. The desiccated lipid cake was subsequently rehydrated with 1 mL of filtered, deionized H$_2$O and stored for up to two weeks at 4° C. LUV effective diameter and polydispersity index were characterized by DLS after rehydration.

Clotting Assays. Clotting was evaluated using a microplate-based assay according to known methods (Smith, et al. (2006) *Proc. Natl. Acad. Sci. USA* 103:903-908) with minor modifications. The citrated plasma was pre-warmed to 37° C. for 20 minutes, and polyP was nanoprecipitated at room temperature and evaluated by DLS before proceeding with the assay. Wells contained 50 µl of citrated pooled normal plasma, 50 µl of polyP NPs in 5 mM CaCl$_2$, 8 mM Tris•HCl, pH 7.4, and coagulation was initiated with 50 µl of 25 mM CaCl$_2$, 75 µM 200 nm LUV (L-α-PC:L-α-PS, 80:20 molar ratio), and 8 mM Tris•HCl, pH 7.4. Final excess free calcium was estimated to be 4.72 mM. Absorbance was read at 405 nm at room temperature on a FINSTRIMENTS Microplate Reader (MTX Lab Systems Inc., Vienna, Va.) every minute for 30 minutes. The sigmoidal absorbance traces were fitted to a standard Boltzmann growth function in Origin Pro 8.6 (OriginLab Corp., Northampton, Mass.). The x-coordinate of the inflection point (parameter x0) was defined as the time at which clotting occurred.

Example 2

Size-Controlled Synthesis of Granular Polyphosphate Nanoparticles

The solubilities of polyP of differing polymer lengths were first investigated by employing DLS. Analogous to determining the critical micelle concentration of a surfactant, the light scattering count rate began to markedly increase when polyP began to precipitate into NPs. The scattering intensity of very long chain polyP (polyP1000+, similar to the long chains in prokaryotes) in aqueous solutions containing various concentrations of mono- and divalent cations was determined. PolyP precipitated in the presence of divalent metal cations at biologically relevant concentrations (5 and 1.2 mM CaCl$_2$, and 1.2 mM CaCl$_2$+ 0.4 mM MgCl$_2$); however, monovalent cations exerted far less precipitative effects than their divalent counterparts. At 5 mM CaCl$_2$, concentrations typical of conventional clotting assays, polyP nanoprecipitated much more easily than at physiological concentrations (1.2 mM CaCl$_2$). K$^+$at normal physiological concentration did not statistically change the scattering intensity profile, while Na$^+$at a relatively high ionic strength of 150 mM combined with 5 mM CaCl$_2$ caused the scattering intensity to increase at a modestly lower monoP concentration. Ca$^{2+}$and Mg$^{2+}$function synergistically to promote nanoprecipitation. The solubility in 1.2 mM CaCl$_2$+0.4 mM MgCl$_2$ was more than 60% lower than in 1.2 mM CaCl$_2$ alone.

Nanoprecipitation was also a function of polymer length, with very long chains (polyP1000+) precipitating much more robustly than intermediate-length polyP (polyP250) or platelet-sized polyP (polyP80) at 5 mM CaCl$_2$. The solubility for each precipitative condition was determined by finding the intersection of the two linear regressions representing molecularly dissolved polyP and polyP NP regimes. The solubilities for polyP1000+and polyP250 at 5 mM CaCl$_2$ were 4.3 and 9.4 µM, respectively, while platelet-sized polyP's solubility at the same condition was about 78 µM. Although not measured, it was expected that polyP80's solubility concentration would be at or above 78 µM in 1.2 mM CaCl$_2$. Upon platelet activation, the concentration of polyP in whole blood can reach up to 2-7 µM (Smith, et al. (2010) *Blood* 116:4353-9), which suggests that platelet polyP likely exerts its procoagulant effects while remaining largely molecularly dissolved. However, the next experiments demonstrate that polyP nanoparticles exhibit dilution hysteresis, keeping open the possibility that polyp granules remain in NP format after secretion from activated platelets, despite being below the thermodynamic solubility limit. In addition, the local concentration of secreted polyP could be orders of magnitude higher than 2-7 µM inside platelet-rich thrombi.

PolyP250 was chosen as a paradigmatic polymer to study nanoparticle stability. First, nanoparticle growth kinetics were examined in an aqueous buffer containing biologically relevant concentrations of ionic calcium for one hour, a time scale approximating a traumatic bleeding event and the half-life of polyP in plasma or serum (Smith, et al. (2006) *Proc. Natl. Acad. Sci. USA* 103:903-908). PolyP250 was nanoprecipitated in 8 mM Tris•HCl, pH 7.4 with 1.2 mM and 5 mM $CaCl_2$. Particle aggregation behavior followed power law kinetics, typical of metastable colloidal dispersions. Initial particle diameters were 169 nm and 58 nm for 5 mM and 1.2 mM $CaCl_2$, respectively. This indicates that the phosphate:calcium ratio may be the major driving force in the thermodynamic equilibrium of polyP nanoprecipitation.

Aqueous buffer is a relatively poor approximation of the environment in circulation as it lacks many of the proteins and peptides that contribute to hemostasis and that regulate pH and plasma ionic strength. In addition to examining the nanoparticle growth behavior in aqueous buffer, stability was also investigated in Tris-buffered suspensions containing 35 mg/ml BSA, to better approximate the conditions found in human plasma. Serum albumin is the most abundant protein in circulation. It binds to a myriad of pharmaceuticals and foreign substances (Sjoholm, et al. (1979) *Mol. Pharmacol.* 16:767-777), tightly regulates serum pH (Van Slyke, eta 1. (1928) *J. Biol. Chem.* 79:769-80), and robustly and competitively binds to metal cations (Pedersen (1972) *Scand. J. Clin. Lab. Inv.* 30:89-94; Pedersen (1972) *Scand. J. Clin. Lab. Inv.* 29:427-32; Pedersen (1971) *Scand. J. Clin. Lab. Inv.* 28:459-69; Foghandersen (1977) *Clin. Chem.* 23:2122-6; Pedersen (1972) *Scand. J. Clin. Lab. Inv.* 29:75-83; Masuoka & Saltman (1994) *J. Biol. Chem.* 269:25557-61) most notably $Ca^{2+}$, $Zn^{2+}$ and $Cu^{2+}$. Due to BSA's functionality, two conditions were considered for polyP250 NP stability: (1) BSA not pre-equilibrated with $CaCl_2$, and (2) BSA pre-equilibrated with 1.2 mM $CaCl_2$. Briefly, 125 µM polyP250 NPs were nanoprecipitated in 5 mM $CaCl_2$ as described herein and mixed 1:1 (v:v) with the BSA suspensions. The particle size evolution was then monitored for three hours. At both salt conditions, the particles immediately shrank from 170-180 nm to approximately 100 nm when they were added to the BSA suspensions. The shrinkage was too rapid to suggest that this was due to enzymatic degradation. Moreover it was not an artifact of multiple scattering or changes in dispersion viscosity (Table 1). PolyP250 NPs in BSA not pretreated with $CaCl_2$ continued to shrink to ca. 50 nm after three hours, whereas the polyP250 NPs in BSA pre-equilibrated with 1.2 mM $CaCl_2$ maintained approximately the same particle diameter, with the final size after three hours being ca. 80 nm. Not wishing to be bound by theory, it is posited that serum albumin may extract $Ca^{2+}$ from the polyP-$Ca^{2+}$ complex.

TABLE 1

| Sample | PolyP250 NP Effective Diameter (nm) | Dispersion Viscosity η* (centipoises) | BSA Volume Fraction (φ) |
|---|---|---|---|
| 125 µM PolyP250 NP in 5 mM $CaCl_2$ buffer | 165.3 | 0.89 | 0.00 |
| PolyP250 NP in BSA (1X = 35 mg/ml) | 100.4 | 1.02 | 0.0531 |
| PolyP250 NP in BSA (2X diluted) | 83.5 | 0.953 | 0.0266 |
| PolyP250 NP in BSA (4X diluted) | 88.0 | 0.921 | 0.0133 |
| PolyP250 NP in BSA (8X diluted) | 86.7 | 0.905 | 0.00664 |

$\eta^* = \eta_s(1 + 2.5\varphi + 6.2\varphi^2)$ for dilute BSA suspensions.

The lognormal particle population was assessed for the following conditions: (1) BSA without $Ca^{2+}$ pre-equilibration; (2) BSA with 1.2 mM $CaCl_2$ pre-equilibration; (3) immediate addition of 125 µM polyP250 NPs to BSA not pre-equilibrated with $Ca^{2+}$; and (4) immediate addition of polyP250 NPs to BSA pre-equilibrated with 1.2 mM $CaCl_2$. BSA without polyP in the presence or absence of calcium displayed two peaks. The first peak centered around 3 nm represented the hydrodynamic diameter of the BSA monomer. The second peak at approximately 15 nm constituted multimeric BSA. The hydrodynamic radius of BSA has been previously reported in the literature to be 3.42 nm (Masuoka & Saltman (1994) *J. Biol. Chem.* 269:25557-61). Quasielastic light scattering data demonstrates that the BSA monomer is a prolate ellipsoid. BSA dimerizes side-to-side, with significant overlap, leading to the dimer being less than twice the size of the monomer (Squire, et al. (1968) *Biochemistry* 7:4261-72).

Addition of $CaCl_2$ has minimal effects on the size distribution of the BSA protein. The particle populations representing conditions (3) and (4) above show that there was an additional peak with a mean diameter of approximately 100 nm. This peak represents the effective diameter of the polyP250 NPs. Moreover, the middle peak representing the BSA dimer had shifted to a larger size, further evidence that polyP may be interacting directly with BSA and forming an adduct mediated by calcium. The striking discrepancy in the hydrodynamic diameter of the polyP NPs in aqueous buffer and in BSA suspension is of interest. Further studies will measure polyP-$Ca^{2+}$ binding constants at these conditions to demonstrate that the evolution in polyP particle diameter, characterized first by a steep drop and then a gradual shrinkage over a time scale of hours, is due to a competitive equilibrium process governed by the differential $Ca^{2+}$ binding affinities of BSA and polyP.

The initial effective diameter of the granular polyP NPs was systemically investigated against the polymer's supersaturation ratio at three different calcium concentrations: 1.2 mM (calcium concentration in human serum), 5 mM (calcium concentration in in vitro coagulation assays), and 7.5 mM. The particle size was plotted against monoP concentrations up to 1 mM for intermediate-length polyP (polyP250). PolyP precipitated in 5 mM $CaCl_2$ at monoP concentrations of 250 µM or greater had to be diluted with more Tris-buffered 5 mM $CaCl_2$ solution before being characterized by DLS (polyP NP diameter is hysteretic after dilution; see Table 2). No trends between particle diameter and monoP concentration were manifested at first glance until the monoP concentration was divided by the solubility of polyP250 at the given calcium concentration and plotted nondimensionally as the supersaturation ratio. At low-to-moderate superaturation ratios (~1-50), the particle size was only a function of the calcium concentration.

TABLE 2

| PolyP250 | Effective Diameter (nm) | Dilution Factor |
|---|---|---|
| 125 µM | 158 | 1 |
| 62.5 µM | 146 | 2 |
| 25 µM | 161 | 5 |
| 12.5 µM | 147 | 10 |

After it was established that the solubility of polyP250 was 9.4 µM in 5 mM $CaCl_2$, 8 mM Tris•HCl, pH 7.4, a sample well above the solubility concentration (in this case 30 µM) was diluted progressively with more 5 mM $CaCl_2$ to decrease the polyP concentration and keep the calcium concentration constant, and the scattering intensity was measured after each dilution. This analysis indicated that the system exhibited hysteresis: the count rate remained much higher even below the solubility concentration despite a thermodynamic driving force for some of the particles to resolubilize. Evidence that polyP NP formation manifests dilution-dependent hysteresis has potentially profound ramifications. For example, a bolus of condensed polyP could be delivered to a trauma site at locally high concentrations and be dispersed further downstream in the circulation without losing its NP format due to its hysteretic behavior, maintaining its associated biological functionality as a procoagulant and proinflammatory agent. However, in human plasma other mechanisms may come into play, such as binding of polyP to membrane-associated proteins on vessel walls adjacent to thrombi, which may prevent polyP NPs from being convected away from the wound site, thereby curtailing a potentially disastrous or even fatal scenario.

It has been found that polyP exerts its most robust procoagulant effects at roughly 10 to 500 µM when assayed at 5 mM CaCl$_2$ (Smith, et al. (2010) Blood 116:4353-9). Indeed, this concentration range almost exactly corresponds to a supersaturation ratio of 1-50 for polyP250 at 5 mM Ca$^{2+}$. However, at physiological calcium concentration, the particle diameter for this polymer length is roughly constant between 36 µM and 1.8 mM. One could speculate that organisms have specifically developed techniques to store and condense polyP in subcellular compartments such as acidocalcisomes and platelet dense granules in a controlled manner by exploiting polyP's roughly constant particle diameter at low-to-moderate supersaturation ratios. Upon secretion, these polyP bodies could potentially serve as concentrated stores of the polymer for biochemical processes requiring rapid, non-linear, or threshold-switchable behavior such as coagulation or quorum sensing.

Transmission electron microscopy was used to examine the polyP particle structure, elemental composition, and morphology. At low magnification, granules appeared spherical in shape and relatively monodisperse, despite the presence of some larger aggregates. The particle diameter was a function of the calcium concentration; inevitably, some aggregation was bound to occur during the drying process and grid preparation. When the particles undergo substantial exposure from the electron beam, the polyP250 NPs develop white spherical spots, resulting in the granules resembling round sponges or soccer balls, despite their uniform electron density. Indeed, using TEM it has been shown that polyP bodies, such as acidocalcisomes and human platelet dense granules, also appear spongy after bleaching with the electron beam, resembling the polyP NPs synthesized herein (Ruiz, et al. (2004) J. Biol. Chem. 279: 44250-7).

At high magnification, the polyP granule was spherical and approximately 200-250 nm in diameter, corroborating DLS data. An X-ray microspectrum of the particle for elemental composition indicated a P:Ca ratio of 67:32, similar to human platelet dense granules (Ruiz, et al. (2004) J. Biol. Chem. 279:44250-7). The P:Ca was 1.76 with trace amounts of K$^+$. However, dense granules are mildly acidic subcellular compartments, which may lead to a different P:Ca stoichiometry, and platelets contain substantial cellular stores of potassium (Zieve, et al. (1964) J. Clin. Invest. 43:2063-9). Potassium was not used herein to precipitate polyP into synthetic polyP granules.

Figure 2:
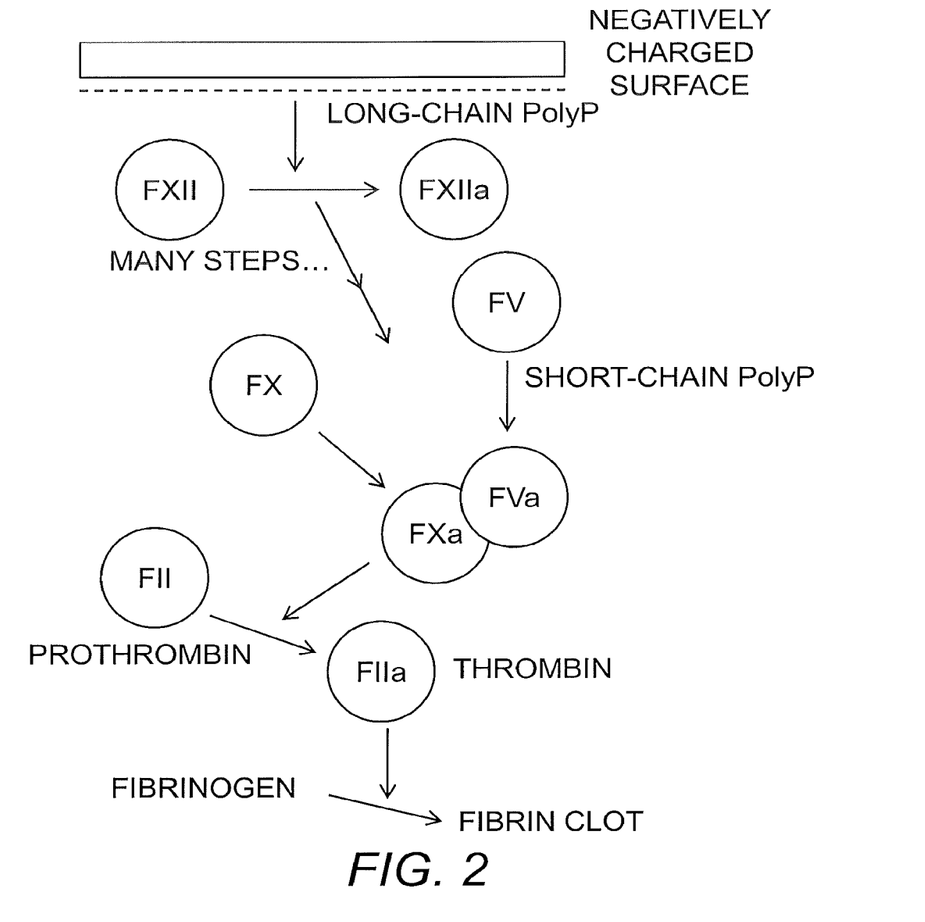
FIG. 2 is a schematic of the intrinsic pathway of blood coagulation. A negatively charged surface (such as the precipitated polyP nanoparticles) serves as the site for assembly of the primary complex consisting of FXII, kallikrein, and high molecular weight kininogen. Molecularly dissolved, long-chain polyP is able to support activation of the contact pathway, while shorter polymer lengths (like those in human platelets) are weak contact activators. PolyP also exhibits procoagulant effects further downstream in the final common pathway of blood clotting.

It has been demonstrated that polyP is a potent activator of the contact pathway of coagulation, and its activity is related nonlinearly with its polymer length (Smith, et al. (2010) Blood 116:4353-9) with long polymers being more robust activators than shorter chains, which exert their effects at different points in the cascade such as via acceleration of FV activation and alteration of fibrin clot architecture and morphology. FIG. 2 shows a schematic representation of the intrinsic pathway of coagulation and the points in which polyP exerts its effects. It is well-accepted in the literature that anionic "surfaces" such as collagen, glass or kaolin are required to form the primary complex composed of FXII (Hageman Factor) and its activation partners, plasma prekallikrein and high molecular weight kininogen (HMWK; Renne, et al. (2012) Blood 120:4296-4303). However, other soluble substances serve as scaffolds for the (auto)activation of FXII. Examples include ellagic acid, lipopolysaccharides, dextran sulfate, and phospholipids (Samuel, et al. (1992) J. Biol. Chem. 267:19691-7). It has been reported that there exists a threshold molecular weight for activation of the intrinsic pathway for polystyrene polymers and dextran derivatives, with contact activity for both polymer types rising sharply at ~25,000 Da (Corretge & Nigretto (1990) Thromb. Res. 59:463-73). Others have communicated that the threshold molecular weight for dextran sulfate is as low as 10,000 Da (Silverberg & Diehl (1987) Biochem. J. 248:715-20).

Previous studies assaying the procoagulant effects of polyp were performed under conditions where the polymer would presumably exist in its molecularly dissolved state. Typically, polyP was incubated together with pooled normal plasma (PNP) for 3-5 minutes prior to recalcification. Since the plasma is citrated, there would be very little ionic calcium available to chelate polyP, and thus no calcium-dependent precipitation would take place. The activation of contact enzymes and the generation of FXIIa are calcium-independent; therefore prior studies investigating polyP's contact activity are confined to an examination of the polymer in the absence of calcium-dependent precipitation. Moreover, plasma contains numerous proteins and peptides such as serum albumin, which may prevent or hinder its precipitation after recalcification. Due to polyP's role in the early stages of natural selection, pre-dating the arrival of polypeptides and quite possibly serving as the precursor to deoxyribonucleic and ribonucleic acid, it is only natural that polyP would serve as the paradigmatic anionic scaffold for serum and cytosolic proteins, emerging as a favored binding partner for peptides with cationic amino acid residues.

Figure 3:
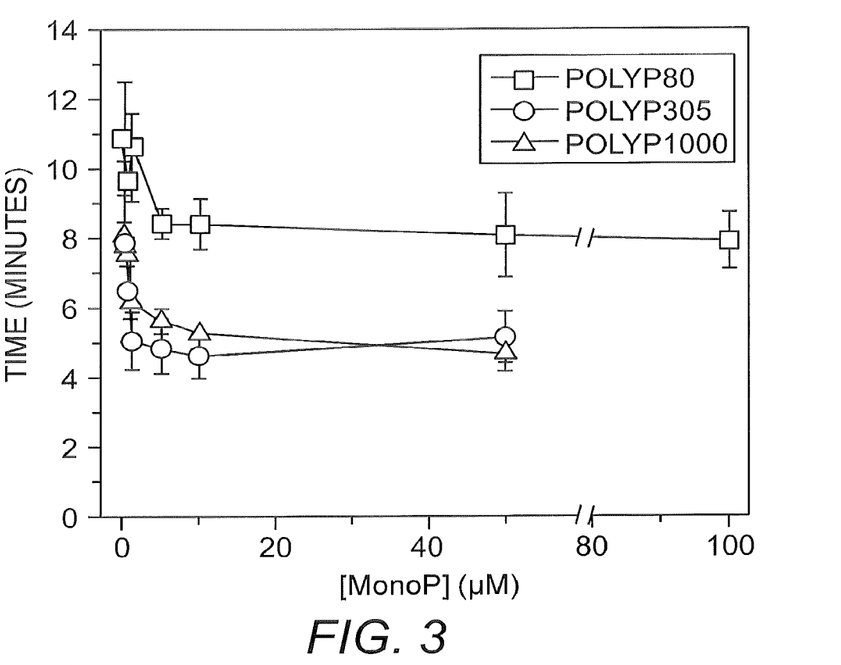
FIG. 3 shows the initiation of the contact pathway by polyP nanoparticles based on polymer length and concentration. Clotting time of polyP is plotted as a function of monoP concentration from 0-100 µM. PolyP was added to 5 mM CaCl$_2$, 8 mM Tris•HCl, pH 7.4 at concentrations above and below its solubility. The presence of precipitated polyP was monitored by dynamic light scattering (DLS) before addition to plasma. Intermediate- and very long-chain length polyP (polyP305 and polyP1000+) are clearly more robust contact activators than platelet-sized polyP (polyP80). The concentration dependence on clotting time for polyP305 and polyP1000+are identical, indicating that a "saturating condition" has been established.

To determine the influence of polymer length and concentration on the activity of polyp, clotting time of polyp polymers or nanoparticles were assayed for contact activity using citrated PNP. The polyphosphates (polyP80, polyP305, and polyP1000+) were first added to 5 mM CaCl$_2$, 8 mM Tris•HCl, pH 7.4 at three times the final assay concentration and characterized by DLS. Once the polyP was incubated with the calcium solution, it was added to the PNP and immediately recalcified to initiate coagulation. Platelet-size polyP (polyP80) weakly shortened time to clot formation, saturating near 10-50 µM monoP. PolyP305 and polyP 1000+, on the other hand, were robust contact activators, drastically reducing clotting times even at sub-micromolar concentrations (FIG. 3). Interestingly, the clotting activities of the two longer polymer sizes were quasi-identical (the error bars overlap for every concentration except one).

These data indicate that platelet-sized polyP only weakly promotes the activation of FXII, with the reduction in clotting time deriving mostly from effects on the final common pathway of clotting. On the other hand, the longer polymer sizes are large enough to serve as scaffolds for primary complex formation after treatment with calcium.

One possibility is that there is a threshold polymer length (molecular weight) (as was previously reported for polystyrene and dextran sulfate) needed to exert the conformational change on the FXII zymogen (or to recruit a sufficiently high local surface density of FXII and its activators). The fact that the concentration dependence is identical for polyP305 and polyP1000+indicates that the nanoparticle solubility is not the threshold condition for contact pathway activation for polymers over the threshold size, as polyP1000+'s solubility is approximately two-fold lower in 5 mM $CaCl_2$. If the solubility were the limiting condition, then polyP1000+'s clotting time would drop at ~4 µM, whereas polyP305's would drop at ~9 µM. However, there are several important caveats that limit the completeness of this analysis: (1) polyP NPs have been shown to exhibit dilution-dependent hysteresis; (2) the solubility of polyP in plasma with its diversity of proteins and peptides and additional polyvalent cations such as $Mg^{2+}$, $Cu^{2+}$, $Zn^{2+}$, $Mn^{2+}$, and $Fe^{2+}/Fe^{3+}$ could be vastly different than in aqueous buffer containing only calcium; and (3) the effect of citrate and other calcium chelators such as EDTA on polyP nanoparticle stability has not been shown.

Regardless of the physical interpretation, the results herein indicate that polyP precipitation under aqueous conditions at physiologic concentrations of calcium and magnesium is a facile means to synthesize large amounts of condensed polyP granules similar in structure to human platelet dense granules for potential downstream uses such as a biocompatible procoagulant agent. In addition, it has now been shown that solubility is related nonlinearly to the polymer length, with very long-chain polyP precipitating much more facilely than platelet-sized polyP. Further, the NP size is only a function of the calcium concentration across a wide supersaturation range. The granules are stable for at least an hour in aqueous buffer solutions, displaying typical power-law growth kinetics, and are stable in BSA suspensions for three hours. Given that the polyP particles are stable on the same time scale as a catastrophic bleeding event indicates that polyP's powerful procoagulant effects on the intrinsic pathway may be related to its precipitation into micron or sub-micron granular particles serving as negatively charged surfaces for FXII activation. The facile, size-controlled synthesis of these particles in the laboratory provides an effective means to mitigate the effects of a diversity of bleeding phenomena such as internal hemorrhage and hemophilia in a minimally invasive manner.

Example 3

Procoagulant Liposomal Formulation

Synthesis and Structure of the Artificial Dense Granules (ADGs). A facile nanoprecipitation process was devised to encapsulate granular platelet-sized polyP into sterically stabilized liposomes rapidly on the benchtop, creating a nanoscale drug delivery platform modeled after the human body's intrinsic arsenal for controlling hemorrhage. The ADGs are composed of a 150-nm granular polyP core surrounded by a 200-nm PEGylated liposome, mimicking the size and structure of human platelet dense granules.

The nanostructure of the ADGs was subsequently examined by imaging and spectroscopic methods. Conventional transmission electron microscopy (TEM) and high-resolution scanning transmission electron microscopy (HR-STEM) were employed to show that the ADGs possess narrow size distribution and a defined core-shell architecture, with a homogeneously dense polyP granule serving as the core and a ring of lighter electron density composed of the phospholipid lamella. Further, electron energy loss spectroscopy (EELS) was exploited to map the ADG's elemental components to prove unambiguously that the synthetic scheme yielded encapsulated polyP particles as intended.

An inherent disadvantage of conventional TEM for structural characterization of biological or biomimetic nanomaterials is radiation damage from the electron beam (Egerton, et al. (2004) *Micron* 35:399-409), limiting imaging resolution to length scales of nanometers and spectroscopy to angstroms (Egerton (2011) *Electron Energy-Loss Spectroscopy in the Electron Microscope*. Springer; Wu, et al. (2013) *Ultramicroscopy* 128:24-31). Standard electron dose and dose rates directed at polyP bodies transform the granular structures into round sponges most likely due to electron beam-induced hydrogen gas bubbling and mass loss; and this therefore necessitates an alternative imaging and structural characterization tool for finer sample elucidation. The ADGs imaged using conventional TEM underscore these obstacles: ADGs display a complex structure in which the finer details of the core-shell architecture are obscured by sample preparation and radiation damage. To overcome these limitations, ADGs were directly sandwiched between two layers of graphene in a biologically compatible manner, before being transferred to the transmission electron microscope (JEOL JEM-ARM200CF) for high-resolution STEM and EELS analysis (Wang, et al. (2014) *Adv. Mater.* 26:3410-3414). The presence of the graphene monolayers has been shown to substantially abrogate the deleterious electronic effects on the sample, minimizing covalent bond cleavage in electron microscopy visualization of biological materials and biochemical reactions of experimental interest (Park, et al. (2015) *Nano Letters* 15:4737-44; Wojcik, et al. (2015) *Nature Commun.* 6:7384; Chen, et al. (2013) *Nano Letters* 13:4556-61; Chen, et al. (2014) *Faraday Discussions* 175:203-14; Kashyap, et al. (2015) *ACS Nano* 8:9097-106). Bare granular polyP NPs prepared in graphene sandwiches are spherical particles of uniform electron density while the characteristic white spots, observed using conventional TEM (Ruiz, et al. (2004) *J. Biol. Chem.* 279:44250-7), are not found. The polyP granules were approximately 150-200 nm in diameter, in very good agreement with DLS measurements. In contrast to the bare particles, the ADGs exhibited a clear core-shell nanoarchitecture characteristic of liposomally encapsulated NPs. A high angle annular dark-field (HAADF) image of an ADG within a graphene sandwich structure reveals a dense, 150-nm core surrounded by an irregularly-shaped 25-nm shell of decreased electron density. These length scales are in good agreement with light scattering data, as the granular polyP NP was measured to have an initial hydrodynamic diameter of ~160 nm, and the sterically stabilized liposomes were formed via extrusion through a polycarbonate membrane with 200-nm pores.

Energy-dispersive X-ray (EDX) spectroscopy has been previously used on isolated dense granules from human platelets and granular polyP NPs to determine their elemental composition and stoichiometry (Ruiz, et al. (2004) *J. Biol. Chem.* 279:44250-7; Donovan, et al. (2014) *Biomacromolecules* 15:3976-3984). EELS is a more powerful tool to map the elemental components of light elements in nanomaterials and has not been used to probe the elemental constituents of human platelet dense granules. Here, the graphene sandwich method was utilized again to prepare ADG samples and the bare particles for EELS mapping in STEM mode, thereby gaining direct insights into the core-shell structure, which was observed in conventional TEM and HR-STEM. The compositional map revealed that the shell structure was composed of C, O, and P, but not Ca, suggesting the presence of a phospholipid envelope. The carbon signal in the shell stems most likely from the PEG brushes and the hydrocarbon tails, glycerol backbone, and headgroup carbons of the phospholipid lamella. The dense core exhibits a homogeneous distribution of Ca, P and O, demonstrating that the granular polyP NPs were successfully encapsulated by the phospholipid envelope. As a control group, the elemental distribution of Ca, P, and O of the bare particle was determined. These elemental maps match well with the acquired HAADF image, and show a uniform distribution of Ca, P and O in the bare particle, consistent with the elemental composition of granular polyP NPs. In order to rule out the possibility that in the ADG, the O and P signals in the core region were only coming from the phospholipid envelope, which also contains O and P, elemental line scans of C, O, P and Ca were performed to show the distribution of these elements. Elemental line scans of C and Ca indicated the presence of a Ca core encapsulated by a ~25 nm thick C shell. The shape of the C and Ca signal was consistent with the typical core-shell structure. Unlike the "saddle" shape of C, which indicates the absence of C in the core, the Gaussian shape of the O and P signals indicated that these two elements were present in both the core and the shell. These line scans demonstrated the absence of Ca in the shell and the absence of C in the core, and showed that O and P were present in both the core and the shell. Furthermore, analysis of the P K-edges was used to compare the local P bonding between the core and the shell. Both spectra showed a near-edge fine-structure typical for $P_xO_y$, while the P spectrum from the shell showed an additional pre-peak, indicating a loss in P—O bonding. These EELS data were consistent with the expectation of the P bonding structure in the granular polyP core as well as the liposome shell.

Figure 4:
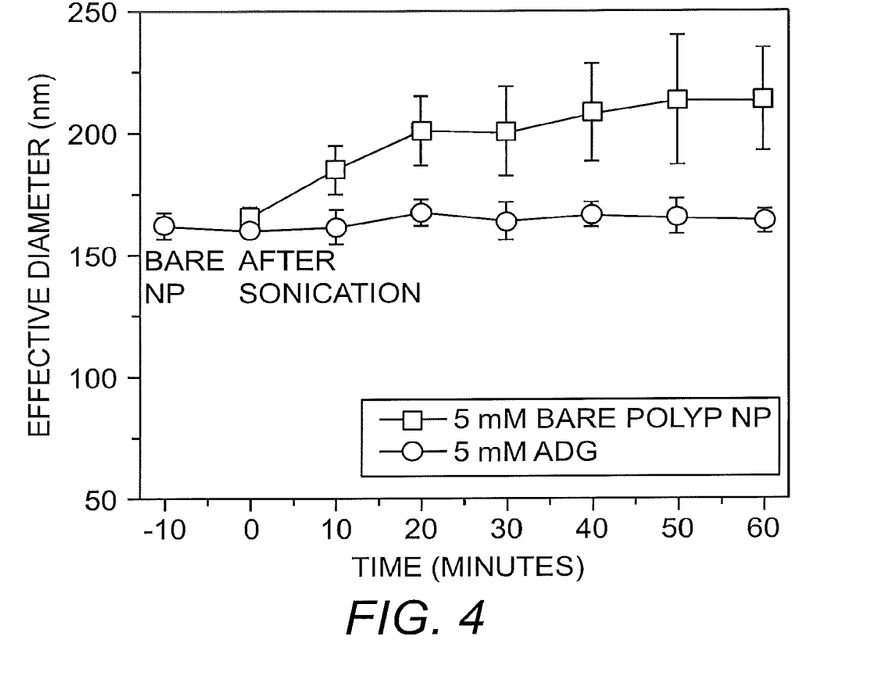
FIG. 4 shows that stability of artificial dense granules (ADGs) in suspension. The average effective diameter was determined for the bare polyP NP (t=−10 minutes), immediately after sonication (t=0 minutes), and every ten minutes thereafter until an hour had elapsed. The ADGs do not appreciably change in size over the duration of the experiment. The bare polyP NPs, on the other hand, prepared at the same supersaturation ratio, grew in a power-law manner to a mean effective diameter of approximately 220 nm in 1 hour.

Stability of ADGs in Suspension. The stability of the ADGs was subsequently investigated for 1 hour at room temperature in the same solvent in which they were prepared (5 mM $CaCl_2$, pH 5.4) utilizing DLS, measured in 10-minute intervals (FIG. 4). The initial effective diameter of the bare polyP granules was approximately 160 nm (t=−10 minutes, FIG. 4). After addition of a stoichiometric excess of sterically stabilized liposomes and 10 minutes of bath sonication, encapsulated polyP granules were monodisperse, with an effective diameter only marginally bigger than their unencapsulated counterparts (t=0 minutes, FIG. 4). Further DLS measurements revealed that the diameter remained unchanged ca. 165 nm after 60 minutes had elapsed, whereas bare polyP NPs in the same solvent environment manifested power-law type growth kinetics. In particular, at the time of nanoprecipitation, the bare polyP granules were approximately 160 nm and quickly ripened to ~220 nm in 1 hour. The equivalent power-law growth phenomenon was clearly absent with the ADGs (FIG. 4). The particle diameter of the ADCs, as determined by electron microscopy, was comparable qualitatively to the hydrodynamic diameter by dynamic light scattering measurements, which indicates that the encapsulated particles observed in HR-STEM were stable in suspension for at least an hour, a time scale sufficient to mitigate bleeding after a severe hemorrhagic event.

Figure 5:
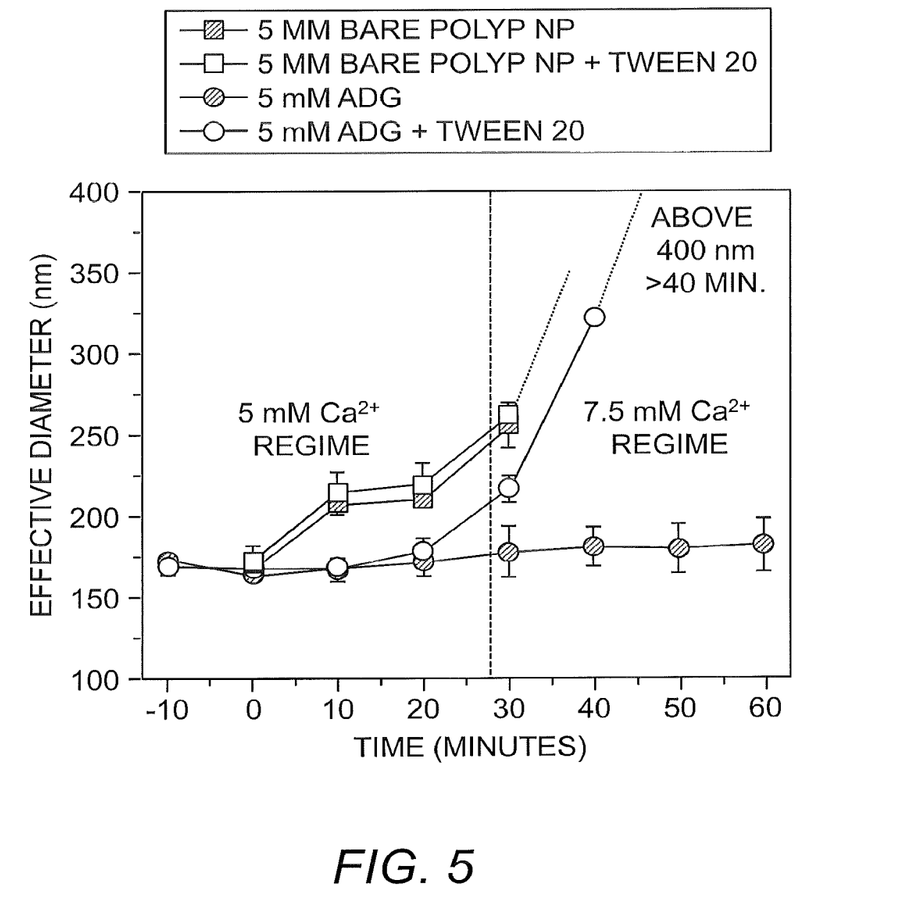

ADG encapsulation efficiency was investigated by modulating the calcium concentration, since the presence of calcium controls the thermodynamic equilibrium of granular polyP NP self-assembly. Changes in the calcium concentration would have nearly immediate effects on the polyP NP effective diameter, as the polyp NP size is solely determined by the calcium concentration over an extensive range of supersaturation values (See Example 2). ADGs (5 mM) were synthesized in 5 mM $CaCl_2$, pH 5.4, and monitored by DLS every 10 minutes. Once 30 minutes had elapsed, the calcium concentration was increased to 7.5 mM and an excess of a non-ionic detergent, TWEEN 20, (which would not affect polyP nanoprecipitation in a measurable way) was added to solubilize the vesicular envelope and expose the polyP cargo to the higher calcium environment (FIG. 5). Upon addition of 0.5% (v:v) TWEEN 20 and increasing the calcium concentration to 7.5 mM, the average particle size rapidly increases above 200 nm (FIG. 5). Ten minutes after detergent solubilization, the particle population was no longer monomodal, with a Gaussian-averaged effective diameter greater than 300 nm. Visible sedimentation of agglomerated granular polyP occurred 20 minutes after adding detergent, with the effective diameter in the micron length scale and the scattering count rate tending to 0. In the absence of detergent and an increase in calcium concentration, in contrast, there was only a negligible change in size, with the average effective diameter centered around 165-180 nm (FIG. 5), comparable to the instance with no modulation in the calcium concentration. Bare polyP NPs subjected to the same experimental scheme showed typical power-law growth before calcium concentration increased and subsequently rapidly precipitated into micron-sized particles after 10 minutes, independent of the presence of detergent. These results indicate that the particle encapsulation efficiency was close to the theoretically maximum value.

Modulating the Procoagulant Activity of ADGs. Not only do the ADGs structurally resemble human platelet dense granules, they can also manifest procoagulant effects in vitro like their biological counterparts when triggering agents are used to disassemble the phospholipid envelope and expose the procoagulant polyP cargo. Inspired by the platelet degranulation process that occurs in vivo, a paradigm is presented through which hydrolytic enzymes present in human platelets or secreted into the circulation after hemorrhage can be exploited to induce clotting factor activity on a time scale sufficient to cease bleeding.

Immediately after traumatic hemmorhage, a concatenation of carefully orchestrated biochemical events must occur near the wound site, with platelets serving as the principal actors in establishing primary hemostasis (Broos, et al. (2011) *Blood Rev.* 25:155-67). Platelets adjacent to the trauma site stick to the damaged endothelium creating a temporary "plug," recruit other platelets via secreted small molecule messengers, and initiate the coagulation cascade by supporting activation of circulating clotting factors (Coughlin (1998) *Arterioscl. Thromb. Vasc. Biol.* 18:514-8; Couglin (2000) *Nature* 407:258-64; Furie & Furie (2008) *New Engl. J. Med.* 359:938-49). PLC plays a major role in platelet activation, and is central to the platelet degranulation process (Brass, et al. (1987) *J. Clin. Invest.* 79:1269-75; Flaumenhaft (2003) *Arterioscl. Thromb. Vasc. Biol.* 23:1152-60); the exocytosis of dense and α granules into the vasculature, ensuring that high local concentrations of polyP are established in platelet-rich thrombi. PLC is an intracellular lipase which hydrolyzes phospholipids at the 3 position (Brass, et al. (1987) *J. Clin. Invest.* 79:1269-75), leading to mobilization of intracellular calcium stores and activation of G protein-coupled secondary messenger systems with diverse physiological consequences extending beyond hemostasis and inflammation (Taylor, et al. (1991) *Nature* 350:516-8). Although PLC in human platelets exclusively hydrolyzes phosphoinositides (Rittenhouse-Simmons (1979) *J. Clin. Invest.* 63:580-7), numerous other PLC isoforms exist in nature that do not discriminate between phospholipids, with many bacterial toxins referred to as "lecithinases" possessing robust PLC activity for phosphatidylcholines and phosphatidylethanolamines (Titball (1998) *J. Appl. Microbiol.* 84:127s-137s; Roberst, et al. (1978) *J. Biol. Chem.* 253:1252-7). These broader-functioning isoforms have been exploited successfully in the past for targeted drug delivery (Duncan (2003) *Nat. Rev. Drug Discov.* 2:347-60).

An additional strategy relies on the presence of secreted phospholipases at sites of inflammation, e.g., around tumors and sites of vascular injury to promote hydrolysis of the vesicular envelope. It has been clinically documented that in human patients with a constellation of inflammatory diseases, such as rheumatism and atheroschlerosis, that the serum concentration of secretory phospholipase $A_2$ ($sPLA_2$) can reach 10-30 ng/mL (Nevalainen, et al. (2000) *Biochim. Biophys. Acta* 488:83-90), with local plasma concentrations in the boundary layer directly adjacent to sites of trauma likely being 100- to 1000-fold higher, approaching 10 µg/mL. Moreover, several studies have shown that degradation of phospholipid vesicles by phospholipase hydrolysis could be an order faster when conjugated to PEG chains (Jorgensen, et al. (2002) *FEBS Letters* 531:23-7). While not wishing to be bound by theory, the likely mechanism is that PEG chains cause extrusion of the phospholipid to the exterior of the bilayer, promoting more rapid and facile phospholipase adsorption at the interface (Majewski, et al. (1997) *J. Phys. Chem.* 101:3122-3129). Therefore, PEGylated phospholid vesicles encapsulating polyP NPs not only offer steric stabilization and immunoprotection, but also a means for controlling and targeting drug release upon phospholipid degredation at the sites where phospholipases are overexpressed.

Figure 6:
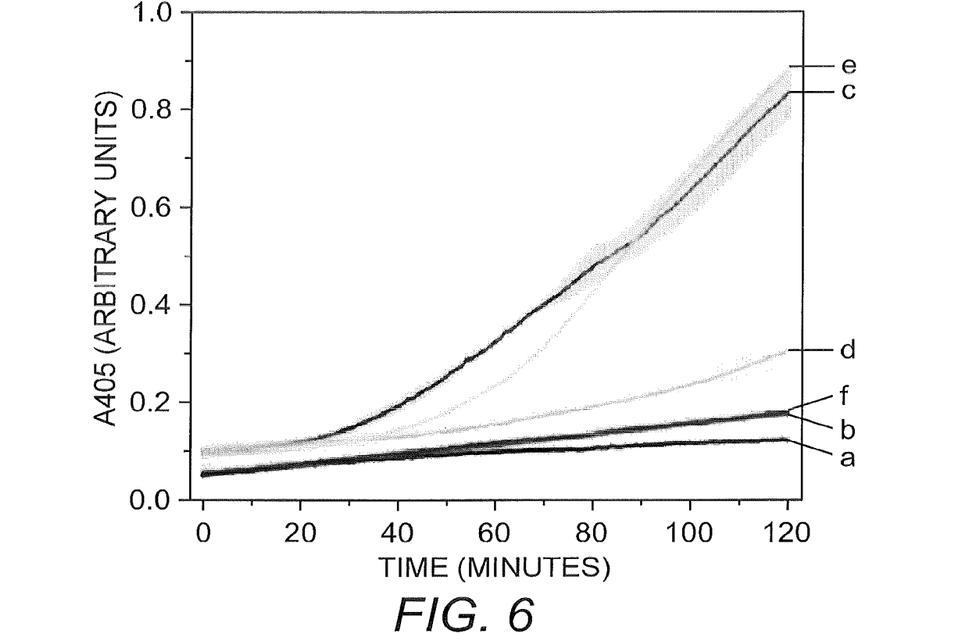
FIG. 6 shows the autoactivation of FXII zymogen via detergent-triggered solubilization of the ADG vesicular envelope. ADGs initiate autoactivation of FXII after addition of 0.5% (v:v) TWEEN 20, similar to the bare polyP NPs (as a positive control). In contrast, ADGs without detergent treatment yield no significant conversion of FXII to FXIIa. As a negative control empty liposomes at the same concentration likewise elicit no FXII autoactivation. a, 5 mM Ca$^{2+}$only; b, 5 mM Ca$^{2+}$+TWEEN 20; c, 500 µM bare polyP NP; d, ADG; e, ADC+TWEEN 20; and f, Empty liposomes.

Before proceeding with phospholipase-dependent clotting factor activity, the ability of ADCs to autoactivate isolated FXII zymogen after detergent-induced solubilzation was assessed as a proof-of-concept demonstrating that the polyP NP cargo retains its procoagulant functionality. There has been limited evidence in the literature that platelet-sized polyP can suitably initiate the contact pathway of blood coagulation, with its procoagulant functions being relegated to the final common pathway (Smith, et al. (2010) *Blood* 116:4353-9). However, as described herein, calcium-dependent nanoprecipitation may alter its contact activity, transforming shorter and intermediate-chain polymers into more robust activators due to the creation of a nanosurface with sufficiently negative zeta potential for presentation to FXII alone or FXII and its activating partners high molecular weight kininogen and prekallikrein. Further, it has been demonstrated that platelet-sized polyP can autoactivate FXII in a manner similar to extrinsic contact activators like dextran sulfate when divalent metals are present (Engel, et al. (2014) *J. Thromb. Haemostasis* 12:1513-22). It has been shown that that platelet-sized polyP robustly supports zymogen conversion (Engel, et al. (2014) *J. Thromb. Haemostasis* 12:1513-22). Similarly, the results presented herein indicate, under similar experimental conditions, that 500 µM ADGs were able to promote autoactivation of FXII after detergent solubilization by 0.5% (v:v) TWEEN 20, whereas ADGs not treated with detergent were largely inert, exhibiting minimal FXII autoactivity (FIG. 6). Empty, sterically stabilized liposomes were also unable to initiate conversion of FXII to FXIIa, suggesting that promotion of autoactivation stems from release of the granular polyP NPs. FXII autoactivity of the bare granular polyP NPs was concentration-dependent, and manifested saturating kinetic behavior with maximal autoactivation occurring at 500 µM monoP for BKGP70, the polyP preparation used in this study.

Figure 7:
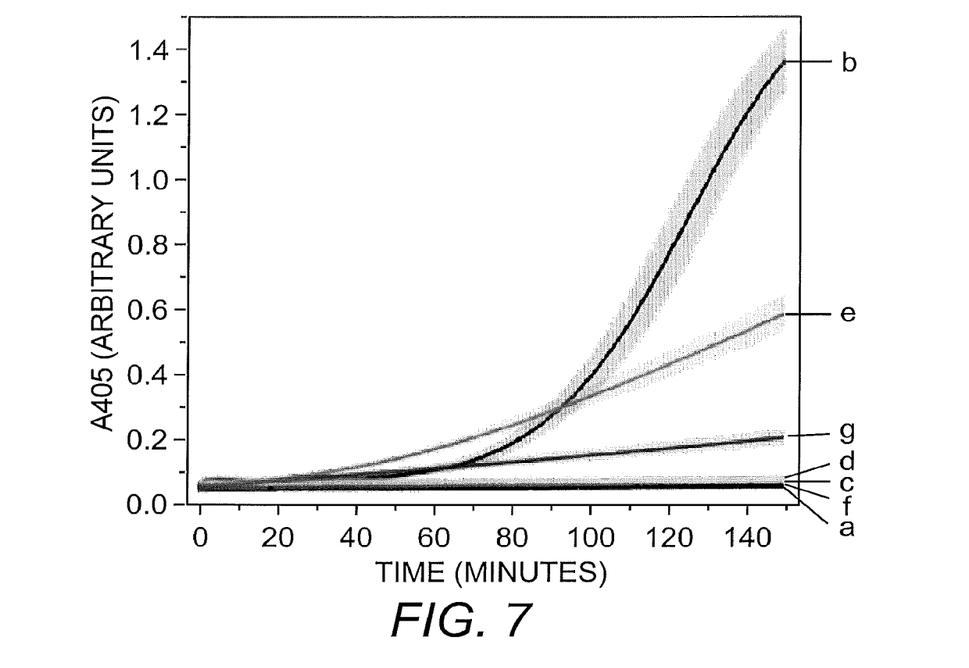

Employing the in vitro microwell plate assay used above slightly modified for phospholipase hydrolysis, the ADGs' effectiveness at initiating FXII autoactivation was assessed under a more biomimetic scenario. ADGs were preincubated in 5 mM $CaCl_2$, 10 µM $ZnCl_2$, 0.1% bovine serum albumin (BSA), 10.6 µg/ml PLC, 5 mM Tris•HCl, pH 5.5 at 37° C. for 20 minutes in the microwell plate before commencement of proteolytic autoactivation of FXII zymogen. The results of this analysis demonstrated that ADCs preincubated with PLC, before addition of zymogen, initiated conversion of FXII in a manner consistent with ADGs subjected to detergent treatment with TWEEN 20 (FIG. 7). ADGs preincubated in the same buffer without PLC were completely "contact inactive." Likewise, empty sterically stabilized liposomes were unable to support autoactivation of FXII zymogen. The absorbance intensity of empty sterically stabilized liposomes preincubated with the equivalent concentration of PLC did increase slightly during the duration of the experiment; however, this rise was likely due to aggregation induced by phospholipid hydrolysis.

Interestingly, 500 µM bare polyP NPs in the presence of 0.1% (w:v) BSA evinced no contact activity over the 150 minute assay, whereas bare polyP NPs without BSA elicited robust FXII autoactivation within 1 hour. Although the autoactivation time was noticeably longer than the previous assay with TWEEN 20, it is important to note that: (1) the polyP NPs were incubated for 20 minutes at 37° C. under different solvent conditions; (2) the proteolytic autoactivation is a nonlinear process, with the kinetics being related logarithmically with time; and (3) another EXIT zymogen preparation was used containing a possibly differing amount of contaminating FXIIa. BSA is an established divalent metal chelator, with low dissociation constants for $Ca^{2+}$, $Zn^{2+}$ and $Cu^{2+}$ (Foghandersen (1977) *Clin. Chem.* 23:2122-2126; Masuoka & Saltman (1994) *J. Biol. Chem.* 269:25557-25561). Moreover, zinc cations greatly accelerate FXII autoactivation, and hence significantly reduce the autoactivation doubling time (Bernardo, et al. (1993) *J. Biol. Chem.* 268:12468-12476; Bernardo, et al. (1993) *J. Biol. Chem.* 268:12477-12483). The presence of millimolar amounts of divalent metals like $Ca^{2+}$ and $Zn^{2+}$ ensures that the predominant polyP species is either a NP or polyp-metal complex. It is well-established that foreign contact activators manifest as either negatively charged colloids or granules like kaolin (Renne, et al. (2012) *Blood* 120:4296-4303) or as polymer-metal complexes, e.g., ellagic acid complexed with copper (Bock, et al. (1981) *Biochemistry* 20:7258-66). The fact that BSA effectively lowers the free ionic concentration of these precipitative divalent metal cations and completely abrogates polyP NP contact activity in this simplified in vitro model of the contact pathway of blood clotting indicates that divalent metal ion complexation to the polymer may be required for polyP to elicit FXII zyomgen autoactivation. Additionally, evidence suggests that polyP is a nonspecific protein binder, facilitating protein folding in a fashion comparable to conventional protein chaperones (Gray, et al. (2014) *Mol. Cell* 53:689-699). Surface plasmon resonance measurements have identified numerous blood proteins that bind to polyP, including thrombin (Choi, et al. (2010) *Biochemistry* 49:9935-41). Indeed, as described in Example 2, bare polyP NPs may complex with BSA via a calcium-mediated process.

It was surprising that enzymatically triggered hydrolysis of ADGs by PLC even in the presence of BSA still yielded significant proteolytic autoactivation, although it was not as robust as bare polyP NPs at the same concentration without BSA. However, the BSA likely chelated ionic zinc present in the assay, which would account for some of the delay. In addition, it was possible that BSA was coating the granular polyP NPs and preventing assembly of the primary complex from occurring. As such, the contact activity of such a polyP-BSA complex may diverge significantly from uncoated polyP NPs due to changes in surface charge density and conformation or macrostructure. Although there is a high concentration of serum albumin in human plasma, polyP still manages to function as a very potent procoagulant agent, implying that the inhibitory effect of serum albumin cannot be too strong. Taken together, these data indicate that PLC hydrolysis of the lipid envelope is occurring, exposing a negatively charged surface to autoactivate the FXII zymogen, and, further, that the sterically stabilized liposome shields the granular polyP NP from interacting with FXII and other proteins like BSA over a duration of at least two hours.

Figure 8:
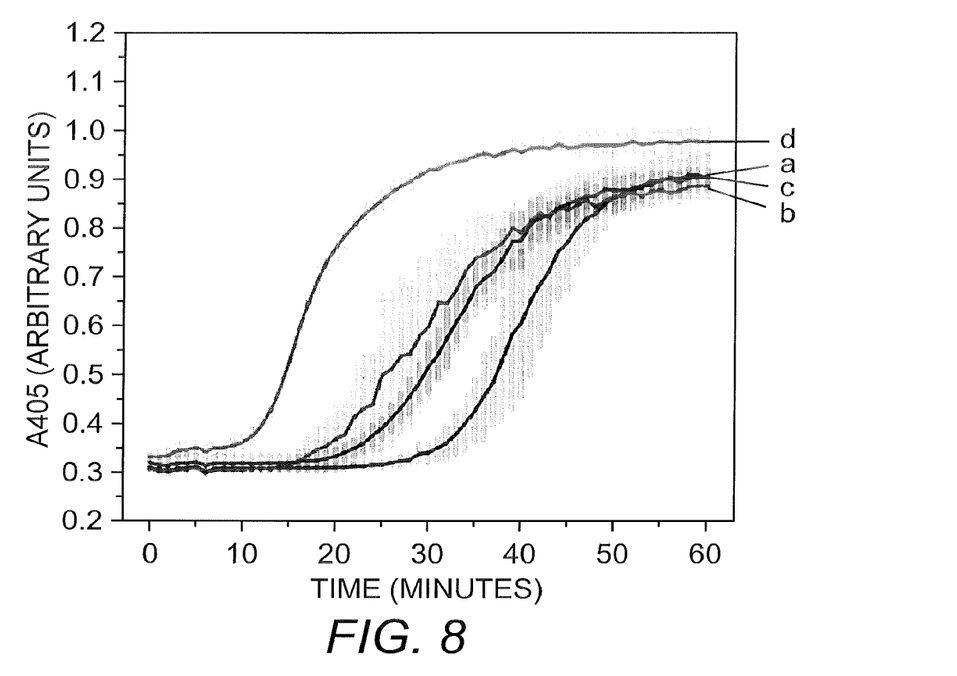

The contact activity of ADGs was also measured in citrated, pooled normal plasma (PNP) in order to investigate the procoagulant efficacy. Prewarmed PNP containing PCPS vesicles was recalcified with 25 mM CaCl$_2$, 5 mM Imidazole, pH 7, and immediately spiked with activator (i.e., no activator as control, 50 µM bare polyP NP, 50 µM ADG, or 50 µM ADG+30 µg/ml PLC). FIG. 8 shows that 50 µM bare polyP NPs modestly initiate the contact pathway of clotting, coagulating around 15-20 minutes, whereas 50 µM ADGs+ 30 µg/ml PLC are excellent contact activators, with a time to initial clot formation at approximately 10 minutes. 50 µM ADGs without trigger shows some procoagulant effect, equivalent to the bare particles, while the control clots in ~30 minutes. As the initiation of the contact pathway is a surface-mediated reaction, the kinetics follow a U-shaped paradigm in which higher concentrations attenuate the procoqulant response by decreasing the colocalization of activating proteins on the same surface. As such, decreasing the phosphate concentration may lower the procoagulability of "ADGs without trigger molecules (such as PLC)" without changing the therapeutic effect of "ADGs with trigger molecules."

What is claimed is:

1. A composition comprising a sterically stabilized liposome shell encapsulating an inorganic polyphosphate nanoparticle core, wherein:
   (a) the sterically stabilized liposome shell comprises polyethylene glycol covalently conjugated to a glycerophospholipid; and
   (b) the inorganic polyphosphate nanoparticle core is prepared by:
   precipitating inorganic polyphosphate under aqueous conditions at physiological pH and salt conditions to form nanoparticles, wherein the inorganic polyphosphate has the structure wherein n is at least 100 and the physiological salt is calcium chloride, thereby producing an inorganic polyphosphate nanoparticle core consisting of calcium, phosphate and oxygen.

2. The composition of claim 1, wherein the sterically stabilized liposome shell further comprises a phospholipid, a sterol, an amine-functionalized lipid or polymer, amphiphilic peptide, polyelectrolyte, amphiphilic copolymer or a derivative or combination thereof.

3. The composition of claim 1, wherein the sterically stabilized liposome shell comprises phosphatidylcholine and 1,2-di-palmitoyl-sn-glycero-3-phosphoethanolamine-N-[methoxy(polyethylene glycol)-2000].

4. The composition of claim 1, wherein the sterically stabilized liposome shell comprises cholesterol.

5. A kit comprising the composition of claim 1.

6. The composition of claim 1, wherein the inorganic polyphosphate nanoparticle core is a precipitated particle of polyphosphate that is between 100 nm and 250 nm in diameter.

* * * * *